United States Patent [19]
Robar et al.

[11] 3,989,009
[45] Nov. 2, 1976

[54] FLUID CONDUCTIVITY MEASUREMENT APPARATUS

[75] Inventors: James D. J. Robar; David G. Glass; Almand O. Barrett, all of Saskatoon, Canada

[73] Assignee: Sed Systems Ltd., Canada

[22] Filed: June 5, 1975

[21] Appl. No.: 584,068

[30] Foreign Application Priority Data

Jan. 16, 1975     Canada .................................... 218016

[52] U.S. Cl. ............................ 119/14.08; 119/14.14
[51] Int. Cl.² ............................................ A01J 7/00
[58] Field of Search ............ 119/14.14, 14.15, 14.08; 324/30

[56] References Cited
UNITED STATES PATENTS

| | | | |
|---|---|---|---|
| 3,664,306 | 5/1972 | Quayle et al. ..................... | 119/14.14 |
| 3,874,337 | 4/1975 | Umbaugh et al. ................ | 119/14.15 |
| 3,878,819 | 4/1975 | Harman ........................... | 119/14.14 |

*Primary Examiner*—Hugh R. Chamblee
*Attorney, Agent, or Firm*—Craig & Antonelli

[57] ABSTRACT

A fluid conductivity measurement apparatus in which the minimum conductivity of one fluid of a group of fluids is determined by comparing electrical conductivities, and the ratios of each of the conductivities to the minimum conductivity are calculated. Where cow's milk is the fluid passing through the apparatus, a determined deviant increase in ratio has been found to be evidence of a high probability of bovine mastitis.

29 Claims, 9 Drawing Figures

FLUID CONDUCTIVITY MEASUREMENT APPARATUS

This invention relates to a system for measuring fluid conductivity, and to indicate when the fluid conductivity is different from a determined value range. The apparatus is particularly useful in the detection of bovine mastitis.

The detection of bovine mastitis, that is, inflammation of the milk secreting tissues of cow udders, has been found to be difficult to perform rapidly as the cow is milked. Samples of milk are usually taken to specialized laboratories, whereupon the presence of mastitis is detected after undesirable delay. Milk showing the presence of mastitis is not deemed suitable for human consumption, and therefore losses of large quantities of milk which have been contaminated by the milk from mastitis infected cows have been experienced. Accordingly, a rapid method for establishing the presence of mastitis has long been needed, by which the presence can be determined directly at milking time. The present invention provides an apparatus for providing such required information, whereupon a cow may be taken out of general production immediately upon detection, which detection occurs at the first sign of mastitis.

It has been found by Robert R. Wolfe et al., as disclosed in the TRANSACTIONS OF THE ASAE, 1972, pages 500–503, that mastitis becomes evident with the detection of high electrical conductivity of milk emanating from an affected quarter of a cow, with respect to the other quarters. A technique for determining the conductivity of milk is described, which uses a dip cell, in conjunction with an impedance bridge, oscilloscope, and audio oscillator set at 1,000 hertz.

Clearly, the described apparatus cannot be used on an on-line basis, due to its cumbersome nature. In addition, dip cell elements have been found to become contaminated, with bacteria and milk compounds, and in turn contaminate and polarize the milk.

A fluid conductivity detector which overcomes the problems of a dip cell is described in Canadian Patent application Ser. No. 211,755, filed Oct. 18, 1974, invented by J. D. Robar et al. The structure is ideally suited for use with the present invention. Contamination does not occur since milk passes through a group of dielectric tubes and does not touch the electrodes. Current is induced in the milk by the use of capacitor plates, whereby the dielectric constant of the milk is used to establish its conductivity. A signal is passed therethrough and is representative in amplitude of the conductivity of the milk. Signals resulting from adjacent tubes are compared, the conductivity ratios are calculated, and the results are provided as an output on an on-line basis. An anomalous increase in conductivity ratio of one or more quarters over the remaining ones has been found to be representative of the presence of mastitis.

It should be noted, that although in this specification the detection of mastitis in milk, or the detection of deviant or increased conductivity from a determined, mean, or minimum value is described, the same apparatus is useful to determine deviant conductivities of other fluids, such as blood, water, etc. The description herein, therefore, is intended to be not limiting to use of the apparatus for detection of conductivity in milk. In addition, while the apparatus is described as providing an indication of conductivity ratios, deviant conductivities, and deviant conductivity ratios, it is clear that the absolute conductivity can be easily calculated and displayed, simply by calibration against known conductivities, and the inclusion of the appropriate output reading device.

The apparatus of this invention for determining deviant conductivity of one or more fluids of a group of fluids from a selected conductivity value, comprises means for providing signals representative of the conductivity values of each fluid, and means connected thereto for comparing the signals and providing output signals representative of predetermined conductivity relationships, depending on the conductivity values, for the fluids.

More particularly, the invention provides an apparatus for detection of the conductivity of fluids comprising (a) a plurality of tubes through which the individual fluids can pass, (b) means for applying a radio frequency signal to each tube in a manner such as to pass through the individual fluids, resulting in individual signals of amplitude representative of the conductivity of each of the fluids, (c) a radio frequency oscillator connected to the (b) means, (d) multiplexing means for combining said individual signals in a predetermined manner connected to the (b) means, (e) detecting means for detecting the amplitude representative of the combined individual signals, (f) demultiplexing means connected to the detecting means for separating the detected individual signals, from the combined individual signals, (g) comparing means for receiving said individual signals and determining the lowest amplitude one of said individual signals, (h) dividing means connected to the detecting means and the comparing means for sequentially determining the ratio of the amplitudes of each of said detected individual signals with the amplitude of the lowest of said individual signals, and providing ratio signals, and (i) means for providing an output from the ratio signals, whereby a ratio deviating in value from the other ratios can be determined.

The invention will now be described in detail, with reference to the drawings listed below, in which:

FIG. 4 is a detailed block diagram of the invention;

FIG. 4A shows how the sheets containing FIGS. 5, 6 and 7 are to be placed together to be read as a single drawing;

Figure 1:
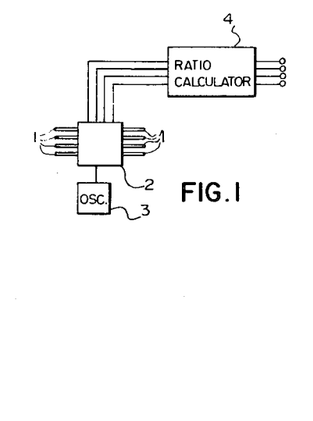
FIG. 1 is a block diagram of the invention in broad form.

Turning first to FIG. 1, a group of tubes 1 is provided through which various streams of fluids are passed. As an example, each of the tubes may be connected to the teat cups in a milking machine, preferably as a by-pass to the main flow of milk from each quarter of the cow. Applied to the tubes 1 is a means 2 for passing a signal through each of the tubes and for providng signals representative of the conductivity values of each fluid. An oscillator 3 is connected to the means 2 for providing the signals, which signals originate from the oscillator 3, and are modified by the dielectric loss or other electrical parameters affecting the conductivity of the milk or other fluid flowing in each of the tubes 1.

The individual signals representative of the fluid conductivities are then applied to a calculating means 4. The calculating means compares the signals, and provides output signals representative of predetermined conductivity relationships, depending on the conductivity values, for the fluids.

While any relationship, or absolute values, can be established by the calculating means for the specific application desired, in the application of the detection of mastitis in milk, conductivity ratios are calculated of each conductivity with respect to the lowest-valued conductivity. Accordingly, in this application the calculating means will comprise means for determining the minimum conductivity, and for calculating the ratio of each of the conductivities with respect to that value.

An output signal is provided which is representative of the calculated values. The output signal can be used to provide graphical information on an oscilloscope, oscillograph, meter display, a light bulb display, or the like.

Accordingly, the invention provides an on-line determination of the conductivity of fluids passing through the tubes 1. In the mastitis detection application, a deviant high conductivity ratio has been found experimentally to be an indication of the presence of mastitis. In a series of tests, a deviant high conductivity ratio of 20 percent in a group of Holstein cattle was shown to be evidence of the existence of mastitis. Since the conductivity ratio is determined in this invention during milking, the affected cow can be immediately taken out of production, saving the simultaneously provided wholesome milk from other cows and reducing the likelihood of contaminated milk being sold for human consumption.

Figure 2:
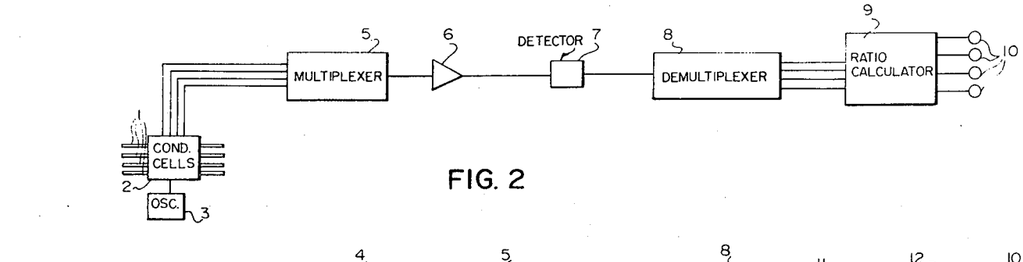
FIG. 2 is a block diagram of the invention in somewhat more detail.

Turning now to FIG. 2, the invention is shown in more detail in block form. As in FIG. 1, means 2 is provided for providing signals representative of the conductivity of fluid passing through the tubes. The aforenoted signals are applied in parallel to a multiplexer 5. The multiplexer combines the signals, and passes them through an amplifier 6 (if needed), to a radio frequency detector 7. The detected signals are then applied to a demultiplexer 8, which separates them into analog form. The analog signals, again representative of the conductivities of the fluids passing through tubes 1 are applied to calculating means 9. As described earlier, the calculating means can determine the absolute conductivity values, determine whether the absolute conductivities are below a predetermined threshold, calculate the ratios between individual conduction values and a selected value (such as the minimum conductivity), etc. Output means 10 connected to the calculating means provides an indication of the calculated value, ratio deviation, etc.

Figure 3:
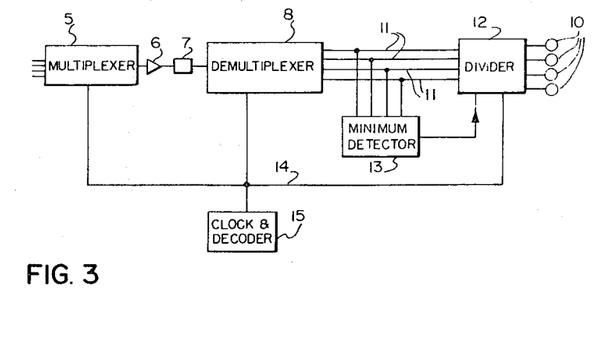
FIG. 3 is a block diagram showing part of the invention shown in FIG. 2 in more detail.

FIG. 3 shows a block diagram of a portion of the invention shown in FIG. 2, in even more detail. In the preferred embodiment the signals are time division multiplexed, the multiplexer 5 being a time division multiplexer, and demultiplexer 8 operating in synchronism therewith. The output from the demultiplexer 8 provides individual signals on lines 11, individually representative of the conductivity values of the fluid in each individual tube. The signals are passed to a divider circuit 12.

Minimum signal detector 13 is also connected to each of the lines 11, and provides at its output, to the divider, a representation of the minimum conductivity signal. The divider performs the ratio calculations as described earlier, and provides at its output signals representative of the ratios of the input signals to the minimum conductivity signal. Output means 10 (optional) are used to display or otherwise indicate the result.

In order that the multiplexer, demultiplexer, and divider work together, they are synchronously enabled from a bus 14, which is actuated by a clock and decoder 15. Accordingly, each conductivity signal is dealt with in timed sequence, repetitively, and synchronously by all of the components connected to bus 14, shown here as multiplexer 5, demultiplexer 8, and divider 12.

Figures 4, 4A:
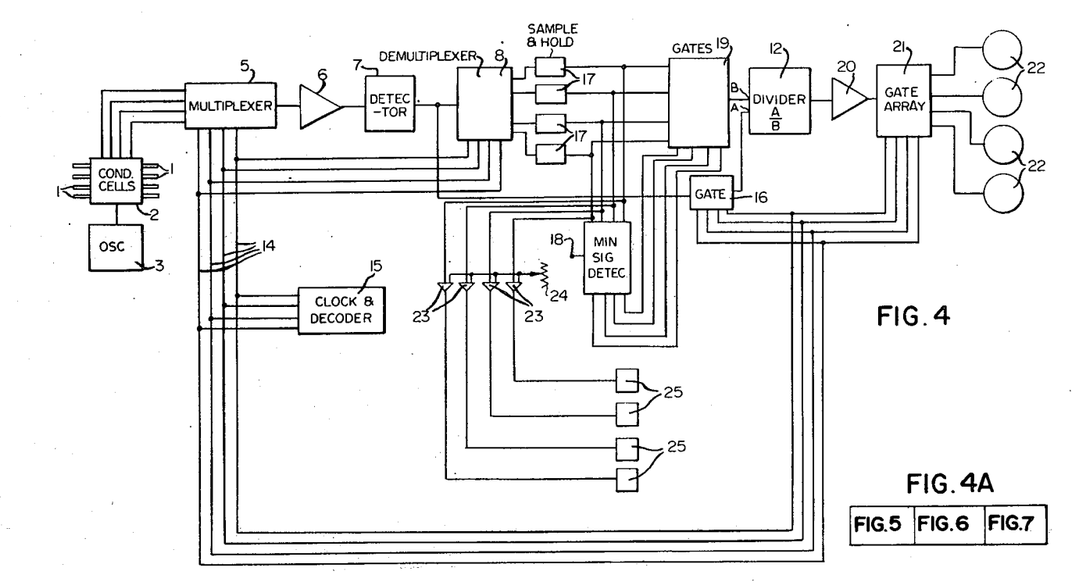

A more detailed block diagram of the invention is shown in FIG. 4. Oscillator 3 applies a signal via the means 2 to the fluid tubes 1. The resulting signals, each representative of the conductivity of the fluid, are applied to multiplexer 5. Preferably the signals are time division multiplexed, and applied through amplifier 6 to detector 7. In the event the fluid to be checked for conductivity is milk, it is preferred that the oscillation frequency be of radio frequency, for instance 9 megahertz and thus the detector 7 will be a video type detector.

The detected signal is then applied to gate circuit 16. Gate 16 sequentially allows each of the detected conductivity signals to pass therethrough, which are applied to divider circuit 12 at input A.

A clock and decoder 15 provides enabling pulses on bus 14, which bus is connected to the multiplexer 5 and gate 16. The gate is thus enabled as described above.

The bus is also connected to demultiplexer 8, which has its input connected to detector 7. Accordingly, the detected conductivity signals are applied to demultiplexer 8, in addition to gate 16.

The output of demultiplexer 8, on individual lines, are representations of the individual conductivity signals, which are applied to sample and hold circuits 17, for each line and conductivity signal. The sample and hold circuits are of the kind which will hold the signals applied to them for the time period between refreshments from the demultiplexer.

The output signals from the sample and hold circuits, representing in analog form again the conductivities of the individual fluids, are then applied to a minimum signal detector 18. The minimum signal detector determines the signal having the least amplitude, and applies an enable signal to one of the lines at its output, which line corresponds to the one carrying the minimum signal. The output of the minimum signal detector is applied to gate circuit 19. The output of the sample and hold circuits 17 is also applied to an input of the gate circuit 19. Accordingly, the enable output signal of minimum signal detector 18 enables only one of the analog conductivity signals applied to the gate circuit 19 to its output: the minimum amplitude signal. This is applied to a second input B of divider circuit 12.

Accordingly, we have sequentially, in analog form, signals representative of the conductivities of each of the fluid streams traversing tubes 1, applied from detector 7, through gate 16, to one of the inputs A of divider 12. We also have the selected minimum amplitude one of those conductivity signals applied to the second input B of divider circuit 12 from sample and hold circuits 17, gated through gate circuit 19.

The divider circuit 12 calculates a ratio of the signals. Therefore a series of ratios, in timed sequence with the series of detected conductivity signals, appears at the output of divider circuit 12. This signal is applied through amplifier 20 to a gate array 21, which is also connected to the bus 14. Individual outputs will thereby be enabled in timed sequence with the presentation of the individual ratios as determined in divider 12. The output signals will therefore be representative of the ratio of each individual conductivity to the minimum conductivity signal. These individual ratios can then be displayed by a display means 22, which can be a strip recorder, meters, lights, etc. Indeed, an additional calculation and threshold circuit can be provided to cause an indication device, such as a light, to illuminate only in the presence of predetermined deviations in conductivity ratio.

In the case in which this invention is to be used to detect mastitis in milk producing animals, such as cows, it is desirable to provide means for detecting when substantially all the milk has been drawn from a particular quarter, during milking, and to provide means for releasing the corresponding teat cup, in order to reduce dry milking stress from the teat. Since the teat cup is normally held to the teat by vacuum pressure, release of vacuum will allow the teat cup to drop. Accordingly, a circuit-actuated vacuum shut-off switch (or solenoid) can be desirably incorporated, preferably with alternative operation either by automatic means, or by manual means.

In the circuit of FIG. 4, threshold amplifiers 23, each have one of their inputs connected to the respective outputs of sample and hold circuits 17. The other inputs of threshold amplifiers 23 are all connected to a potential threshold control 24, which is of well-known design, and will not be described in more detail.

The outputs of threshold amplifiers 23 are individually connected to vacuum shut-off switches or solenoids 25.

Accordingly, since the output signals from sample and hold circuits 17 are representations of the conductivity of milk in each of the quarters of the cow, an individual vacuum cut-off switch or solenoid 25 will be caused to operate should the conductivity of a particular quarter drop below a predetermined threshold as set up in the threshold control 24. Should the milk suddenly deplete from a particular quarter, the indicated conductivity will drop substantially, and the corresponding vacuum switch 25 will cause cut-off of the vacuum to the teat cup, releasing it from the teat and stopping its milking action. The threshold can be set at, for example, 50 percent conductivity.

Figure 5:
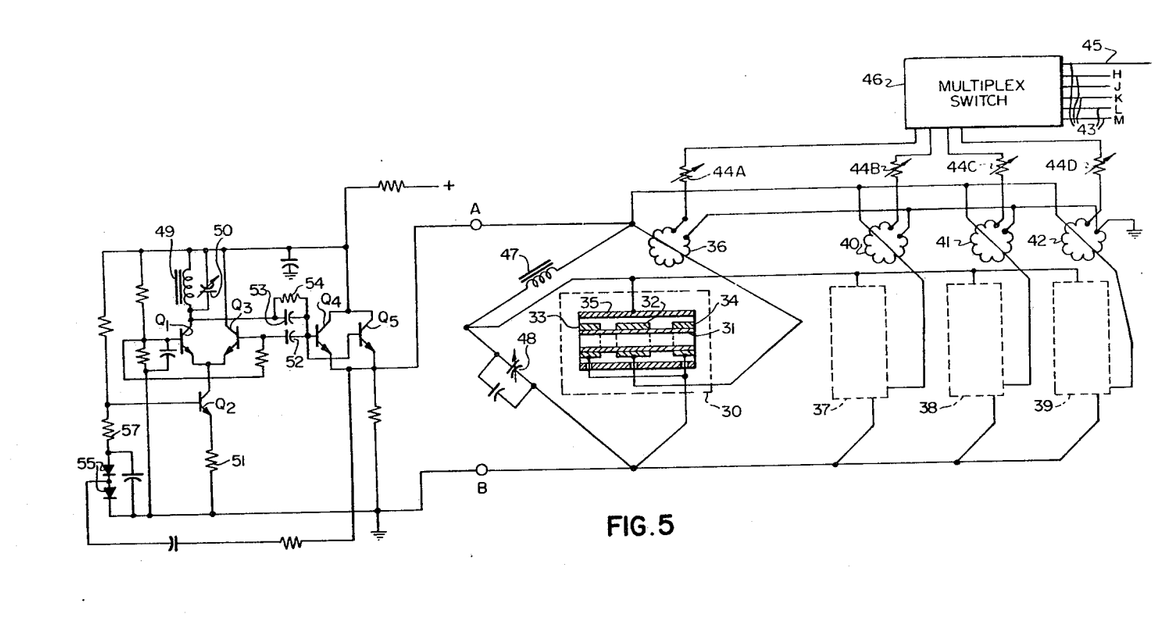
FIGS. 5, 6 and 7 are detailed schematic drawings of the major portion of the invention.
Figure 6:
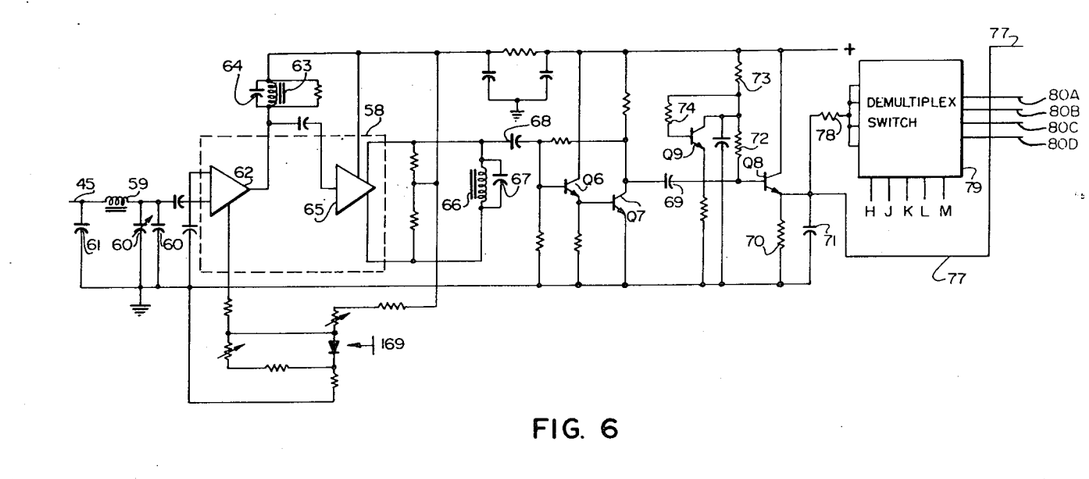
Figure 7:
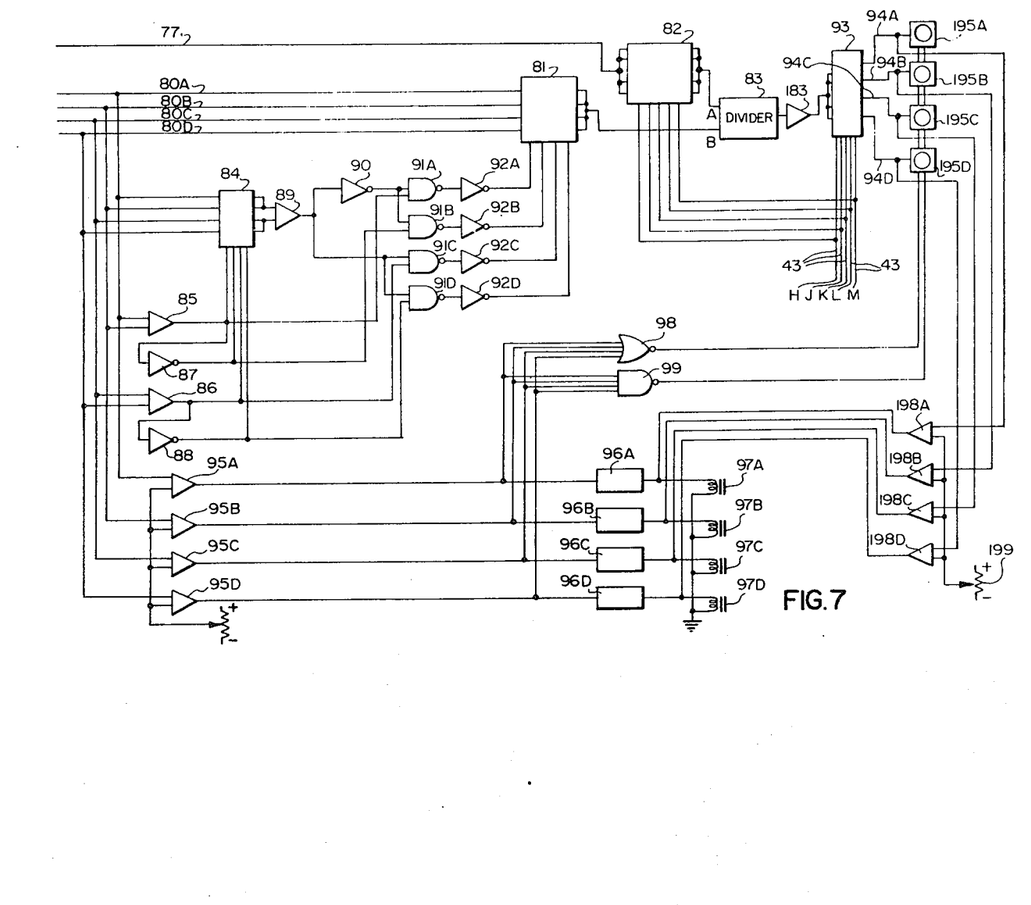

A preferred embodiment of the specific circuit will now be described in detail. FIGS. 5, 6 and 7 should be assembled as shown in FIG. 4A.

Turning to FIG. 5, centrally of the page one of the conductivity sensors 30 through which one stream of fluid is passed is shown in section within the dashed line. The conductivity sensor comprises dielectric tube 31 through which the fluid is passed. A conductive cylinder 32, which forms one electrode of a capacitor, surrounds the tube. Conducting cylinders 33 and 34 are laterally spaced along the axis of the tube, and are connected together, forming counter-electrodes of the capacitor. Fluid flowing through dielectric tube 31 provides the major dielectric of the capacitor. Accordingly, an a.c. signal applied across the capacitor will be modified in amplitude by the conductivity of the fluid.

Surrounding, and insulated (as by air spacing) from the conductive cylinders 32, 33, and 34 is guard electrode 35 in the form of a cylinder. The guard electrode should extend past each end of the conductive cylinder 32 by at least 25 percent of the length of the latter cylinder.

Signal is applied from an oscillator at terminals A and B. It may be seen that the electrode 32 is connected to terminal A and electrodes 34 and 33 are connected to terminal B.

The conductor leading to electrode 32 is caused to pass through toroid 36, the conductor forming a one turn primary winding and toroid 36 forming a secondary winding of a transformer from which an output signal is obtained. The secondary winding of the transformer, in the present example, preferably has 11 turns. The frequency of the input signal at terminals A and B preferably is approximately 9 megahertz.

Connected in parallel with conductivity sensor 30, are conductivity sensors 37, 38, and 39. However, the corresponding central cylinders or center electrodes of the latter conductivity sensors are separately brought together as one turn transformer primary windings through toroid secondary windings 40, 41, and 42. Accordingly, all the conductivity sensors 30, 37, 38, and 39 will receive a signal from the oscillator, via terminals A and B, and the signal amplitudes traversing each individual sensor will be induced in toroid windings 36, 40, 41, and 42. The amplitudes of the induced signals will be dependent on the conductivity of the fluid traversing dielectric tube 31 and the corresponding tubes in sensors 37, 38, and 39.

One terminal of each of the toroids 36, 40, 41 and 42 are connected together and to ground. The other terminal is connected to a multiplexer 46, corresponding to multiplexer 5 of FIG. 4. The multiplexer can be comprised of a pair of CD4016 type quad bilateral switches, available from Radio Corporation of America. The switches are individually enabled in sequence from multiplex bus 43, at conductors referenced as H, J, K, L, and M.

In order to calibrate and adjust the signals from the conductivity sensors, variable resistors 44A, 44B, 44C, and 44D can be used in series with the respective conductors leading from each of the toroids to the multiplex switch. The multiplex switch is connected in a well-known manner, and will not be described further. However, the combined, time division multiplexed output signal is obtained at conductor 45.

In order to minimize the effect of stray ground loop current paths and leakage paths through stray capacitances, an inductance 47 is connected between terminal A, that is the common meeting point of the conductors leading from one conductive cylinder of each of the sensors, through the individual torioids, to all of the guard shields 35 in parallel.

The guard shields are also connected to terminal B through a variable capacitance 48, which can be bypassed by a fixed capacitance (not referenced). Upon application of signal, the variable capacitance is varied until the output signal from the group of sensors in minimum. In other words, the capacitor 48 (or inductance 47 in conjunction) is tuned for a null.

Turning now to the radio frequency oscillator, preferably operating at 9 megahertz for the measurement of milk conductivity, any buffered oscillator which will properly drive the multiplex switch can be used. For completeness of this description, an exemplary oscillator which may be used with the present invention will be described.

The oscillator is comprised of NPN transistor Q1, having a tuned circuit comprising the parallel arrangement of inductor 49 and capacitor 50, connected in series with its collector, to a source of potential +. The capacitor preferably is variable, in order that the frequency of oscillation could be changed.

Connected in series with the emitter of transistor Q1 is the collector-emitter circuit of transistor Q2, which has its emitter connected to ground through a resistor 51. Appropriate and well-known biasing and decoupling resistors and capacitors are also connected as shown, but are not referenced.

NPN transistor Q3 has its emitter conneccted to the emitter of transistor Q1, and its collector connected to a similar source of potential as transistor Q1. The base of transistor Q3 is connected through a coupling capacitor 52 to the base of NPN transistor Q4, the latter being connected directly in parallel with similar transistor Q5.

The base of transistor Q4 is connected to the collector of transistor Q1 through the parallel arrangement of capacitor 53 and resistor 54. An automatic gain control function is obtained by feeding the signal appearing at the emitter of transistor Q4 back through an unreferenced resistor and capacitor in series to the junction of a pair of clipping diodes 55 and 56. The output signal is thus rectified and fed back as a D.C. base potential foro transistor Q2, through resistor 57. Since transistor Q2 provides emitter loading on transistor Q1, the effective load is modified by the amount of fed back D.C. potential. Accordingly, a constant output signal amplitude is obtained.

The remainder of the decoupling capacitors and resistors in the oscillator circuit leading to the source of potential (positive, in the case of the NPN transistors shown), and ground, the between terminals A and B are well known in the art, and will not be discussed in detail here. However, it may be noted that the transistors in the oscillator may be obtained as type CA3086 transistor array, from Radio Corporation of America.

Turning now to FIG. 6, the amplifier 6, detector 7, and demultiplexer 8 described with reference to FIG. 4 is shown in more detail.

The preferred heart of the amplifier 6 is comprised of part number $\mu$A757 Gain Control Amplifier, available from Fairchild Semiconductor, and is shown generally in dashed line as reference numeral 58. The input of the amplifier is tuned, being connected with inductor 59 in series, and capacitor 60 (which usefully can have a variable component) in parallel. The input to inductor 59 is connected to the conductor 45 which carries the multiplexed output signal from multiplex switch 46. A capacitor 61 connects conductor 45 to ground, to which the capacitor 60 is also connected.

The output of the first stage 62 of the amplifier 58 is tuned by its series connection through the parallel arrangement of inductor 63 and capacitor 64, to a decoupled source of potential +. The output of the second stage 65 of amplifier 58 is tuned by a series connection to the parallel arrangement of inductor 66 and capacitor 67. The tuned output is taken through coupling capacitor 68 to a driver stage for the detector which follows.

Gain in amplifier 58 is controlled through a well-known circuit shown generally by reference numeral 169, which will not be described further.

The signal from capacitor 68 is applied to the base of NPN transistor Q6, the emitter thereof being connected to the base of NPN transistor Q7. The collector of transistor Q6 is connected to a source of potential +, and the emitter is connected through a load resistor to ground. The collector of transistor Q7 is connected through a load to the source of potential +, and its emitter is connected to ground. The base of transistor Q6 is connected to a source of potential + and to ground through well known resistive means, and will not be described further.

The output of transistor Q7 is connected through coupling capacitor 69 to the base of NPN transistor Q8. Transistor Q8 is connected as an emitter follower, having its emitter connected to ground through load resistor 70, by-passed by capacitor 71, which latter network by-passes radio frequencies to ground.

Connecting the base of transistor Q8 to a source of positive potential is the series arrangement of resistors 72 and 73. The collector of an NPN transistor Q9 is connected, to their junction, as is resistor 74, which is also connected to the base of transistor Q9. The emitter of transistor Q9 is connected through resistor 75 to ground.

In operation, transistor Q9 and its accompanying circuitry operates as a temeperature compensated forward bias control for Q8. The base-emitter function of Q8 is the forward biased diode for a detector. The resulting detected signal envelope is of similar character to the original conductivity signals, wwhich are linear in form, but also are serially time multiplexed.

Capacitor 76, connected between the collector of transistor Q9 and ground, with resistor 72, and also capacitor 71 and resistor 70 perform the low pass filtering required.

From the emitter of Q8, an all-channel signal output is obtained at conductor 77. Conductor 77 corresponds to the output of detector 7 in FIG. 4, which is connected to gate 16.

In addition, the output signal is passed through resistor 78 to demultiplexing switch 79, which corresponds to demultiplexer 8 in FIG. 4.

Terminals H, J, K, L and M are connected to the multiplex bus 43, described earlier, which bus is connected to the demultiplexing switch 79. The output of switch 79 is shown at terminals 80A, 80B, 80C, and 80D, which correspond to each individual conductivity signal channel.

The demultiplex switch may be obtained as part number CD4016 quad bilateral switch from Radio Corporation of America.

As shown in FIG. 4, the signals are then passed to sample and hold circuits 17. Each sample and hold circuit can usefully be comprised of the amplifier described in Radio Corporation of America Linear Integrated Circuit Data Book SSD 201B, page 221. However, it is preferred to increase the gain of that circuit by well-known means approximately by five times. This can be done by providing Miller Effect compensation capacitance, and internal positive feedback (but not to the point of oscillation) in a well-known manner.

Turning to FIG. 7, the output signals of each of the sample and hold circuits are then applied to gate circuit 81, which corresponds to gate circuit 19 in FIG. 4. Similarly, the combined signal, on conductor 77, is applied to gate circuit 82, which corresponds to gate circuit 16 in FIG. 4. Both gate circuits 81 and 82 can be part number CD4016 quad bilateral switches, available from Radio Corporation of America. The gate circuits have four input terminals, those of gate circuit 82 being connected together to conductor 77. Gate circuit 82 is enabled via multiplex bus 43. The output of gate circuit 82 is therefore the detected conductivity signals in time series. This signal is applied to input terminal A of dividing circuit 83. The output of gate circuit 81 is applied to input B of dividing circuit 83, where a ratio calculation is performed.

The following will describe circuitry for obtaining the signal at B corresponding to the minimum amplitude conductivity signal.

Quad bilateral switch 84 has its inputs respectively connected to each of the signal conductors 80. Operational amplifier 85 has its two inputs respectively connected to two of the conductors 80A and 80B, and operational amplifier 86 has its two inputs connected to the other two of the conductors 80C and 80D. Both of the aforenoted operation amplifiers, which operate in a comparator mode, and which can be code number LM324 quad operational amplifiers, are available from National Semiconductor. Their outputs are connected to two of the gate enable inputs of the guad bilateral switch 84. They are also respectively connected to inverters 87 and 88, the outputs of which are connected to the other two gate enable inputs of switch 84. Accordingly, the gate enable inputs of switch 84 will be enabled under the following conditions, by successive inpputs: the amplitude of the second line being greater than the first, the amplitude of the first line being greater than the second, the amplitude of the fourth line being greater than the third, and the amplitude of the third line being greater than the fourth.

Two signals of the four appearing in conductors 80A, 80B, 80C and 80D will therefore be enabled to pass through quad bilateral switch 84, which are then applied to operational amplifier 89 which operates in a comparison mode. The output of amplifier 89 will be an enable signal when the conductivity signal on the first or second lines is greater than that at the third or fourth. Inverting amplifier 90 provides an output enable signal when the inverse amplitude relationship exists.

A group of four NAND gates 91A, 91B, 91C, and 91D each have a pair of inputs, one of each being respectively connected to the outputs of amplifiers 85, 86, 87, and 88. The other two terminals of the NAND gates connected to the inverting amplifiers 87 and 88 are connected together and to the output of operational amplifier 89. The other outputs of the two NAND gates which are connected to amplifiers 85 and 87 are connected together to the output of inverting amplifier 90. The outputs of the NAND gates 91A, 91B, 91C and 91D are applied to inverting amplifiers 92A, 92B, 92C, and 92D respectively, resulting in an enable signal at the output of the inverting amplifier 92A–92D which corresponds to the line carrying the smallest amplitude conductivity signal. The latter outputs are connected to the enable inputs of gate circuit 81. This will cause the minimum signal applied thereto to be enabled and pass through gate circuit 81. Accordingly, the output of gate circuit 81 comprises a single analog signal corresponding to the minimum conductivity signal received from the conductivity sensor. This is applied to the dividing circuit 83 at input B.

The operational amplifiers 85, 86, and 89 can be code number LM324 quad operational amplifiers available from National Semiconductor. Inverters 87, 88, 90, 92A, 92B, 92C, and 92D can be code number CD4049 hex inverter, and available from Radio Corporation of America. NAND gates 91A, 91B, 91C and 91D can be code number CD4011 quad two input NAND gates available from Radio Corporation of America. In addition, dividing circuit 83 can be the circuit described in the Motorola Linear Integrated Circuits Data book, 3rd edition, February 1974, page 8–395. The operational amplifier MC1741G in that circuit alternatively could be the Fairchild operational amplifier $\mu$ A741, with the load circuit $R_L$ changed to 560 K ohms.

The signals appearing at inputs A and B of the dividing circuit 83, consisting respectively of an analog representation of the conductivity signals, in time sequence, and the minimum conductivity signal, are divided, resulting in signal representing their ratios, in time sequence, appearing at the output of dividing circuit 83. The signal appeeearing thereat is applied to operational amplifier 183, where it is inverted, and applied to quad switch 93, which corresponds to gate array 21 in FIG. 4. The quad switch is connected to multiplex bus 43, the signal on which causes each of the ratio signals to be applied sequentially to respective outputs 94A, 94B, 94C and 94D. The ratios are displayed on indicators 195A, 195B, 195C and 195D, which can be respective channels of a strip chart recorder or the like, a threshold detector with a light or audible warning, etc.

For the measurement of conductivity of milk, it has been found that while the absolute conductivity for various cows is different, the normalization of ratios of their conductivities to the lowest conductivity shows a fairly close conformity. However, an increase in conductivity ratio above the normal variations has been found to be evidence of bovine mastitis in the quarter showing the high conductivity ratio.

Since this determination of abnormal ratio is made in real time, it can be used as a control function and for record keeping; for example, to divert abnormal milk and to record the incidence of disease.

As was mentioned earlier, it would be useful to obtain an indication when conductivity drops below a predetermined threshold, in order to provide means for removing the teat cup from the quarter which has been depleted. Operational amplifiers 95A, 95B, 95C, and 95D each has one input connected to a respective line 80A, 80B, 80C, and 80D. The other inputs all connected together, to a potential reference. In the event an output drops below the equivalent reference threshold which has been set, an output signal from the operational amplifier will occur.

The outputs of the operational amplifiers are individually connected to timers 96A, 96B, 96C, and 96D, which provide an output signal after a set time delay. In the present embodiment, a 20 second delay has been found to be useful, in case the cow has been "holding back" in a particular quarter for a brief interval. After passage of the 20 second delay, an output signal is passed to the corresponding solenoid 97A, 97B, 97C, and 97D, of vacuum shut-off switches which are within the vacuum circuits of the teat cups. Of course, multiple timers tuners can be used to provide indication or operation after different time intervals.

In addition, NOR gate 98 and NAND gate 99, each have four input terminals, connected to the respective outputs of operational amplifiers 95A to 95D. The output of NOR gate 98 is connected to inhibit inputs of indicators 195A–915D, and the output of NAND gate 99 is connected to reset inputs of the indicators. Accordingly, should any of the quarters become dry, the indicators will be cut off from displaying new measurements, since the minimum conductivity will be erroneously low or zero. On the other hand, when no output appears from one or more of the operational amplifiers 95A–95D, at least one of the four quarters will be producing milk, and NAND gate 99 will not reset the indicators, whereupon the most recent valid ratio output signal will be displayed.

In addition to removing milking vacuum at end of milking, it may be desirable to remove vacuum to any or all quarters which indicate conductivity ratios above a value predetermined as normal. The operational amplifiers 198A, 198B, 198C and 198D effect this operation by comparing the signal voltages at outputs 94A, 94B, 94C and 94D by switching to a high state when any or all of these signals are above the threshold set by threshold potentiometer 199, to which they are all connected. This switching action energizes the appropriate solenoid 97A–97D and the vacuum is thereby removed.

Vacuum can also be removed simultaneously from all four quarters after the last quarter has been depleted. This is effected by connecting the output of the NAND gate 99 in parallel with the input lines to the timers 96A, 96B, 96C and 96D after said inputs have been decoupled from operational amplifiers 95A, 95B, 95C and 95D.

Considering now the multiplexing circuitry with respect to FIG. 4, in particular clock and decoder 15, a 200 hertz clock such as part number CD4001, available as a quad two input NAND gate from Radio Corporation of America is connected in a well-known manner with appropriate positive feedback to provide a 200 hertz signal. This is applied to a dividing circuit, such as code number CD4017 decade counter and divider available from Radio Corporation of America, to divide the 200 hertz signal by five, and apply it to the multiplex bus 14 (i.e. 43) to sequentially enable one of the lines in the bus at a 40 hertz rate. Accordingly, it will be seen that the quad switch 93, gate circuit 82, demultiplex switch 79, and multiplex switch 46 in FIGS. 5, 6 and 7 will all be operated in synchronism.

For the use of this invention directly in conjunction with a milking machine, it is desirable that automatic and manual shut-off of the milk orifices be provided, whereby milking suction is removed when the quarter of the cow becomes substantially depleted or dry, or upon election by the operator, the former will operate automatically in response to the actuation of one or more of solenoids 97A, 97B, 97C and 97D, which has been described earlier as operating once a substantially reduced conductivity is detected. The solenoids can operate in conjunction with a valve structure such as shown in section in FIG. 8.

Figure 8:
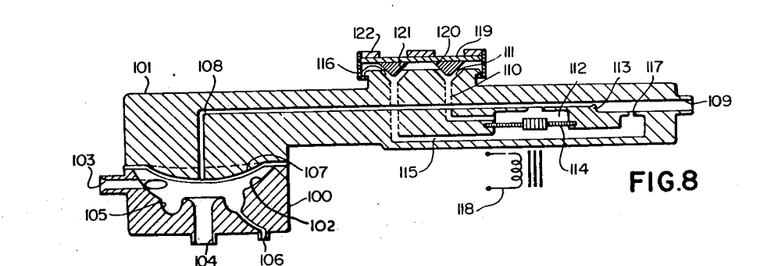
FIG. 8 is the cross section of a fluid valve mechanism.

The valve structure comprises two parts, the valve proper 100, and a control section 101.

A bowl, or hollowed out portion 102 is provided in the valve 100 into which communicates an inlet orifice 103. Multiple inlet orifices may be provided as required.

An outlet orifice 104 is provided in bowl 102 to which, during operation, suction is applied and from which egresses the controlled fluid. Multiple output orifices may be provided.

A depression 105 (or depressions) may be provided in the bottom of bowl 102. This may in turn be connected to a second outlet orifice (or orifices) 106 which is in turn connected to vacuum.

The bowl portion 102 of the valve 100 is preferably circular in form. The inlet into the bowl may be set at an angle to cause a swirling action of the fluid in the bowl. In addition, the depression 105 may be ring shaped and generally surrounding and depressed from the orifice 104.

Outlet 106 may be set at such a position as to take advantage of the circulating action in depression 105 to control flow rate through orifice 106 or to influence the portions of a mixture of substances of differing densities flowing through orifice 106.

Since the swirling liquid flows through orifice 106 under the influence of centrifugal force, the valve is not restricted to operate under the action of gravity.

In operation, as a control valve on a milking machine, milking suction (or vacuum) is applied to orifice 104, and a source of vacuum as well to orifice 106. Milk from the cow will enter orifice 103 and swirl around the bowl 102. Milk will enter the ring shaped channel 105, fill it up, and be also passed out by-pass tube and orifice 106. Once milk has filled the channel 105, it will spill over into orifice 104, and out into the mixing bowl of the milking machine claw or the like. During operation, the bowl 102 is substantially filled.

Orifice 106 is connected via a tube directly to the conductivity sensor dielectric tubes which were described earlier. Only a sample of the milk emanating from the quarter of the cow is required to be sampled for conductivity.

In the event there is a short hold-back of milk by the cow, and milk becomes depleted from bowl 102, channel 105 acts as a reservoir for milk passing into the corresponding conductivity sensor, which reservoir therefore evens out pulses of milk, hold-backs, etc., and reduces the likelihood of erroneous conductivity readings due to random and short milk depletions. Accordingly, it should be noted that the width and depth of channel 105 can be altered to suit the expected time delay, and to insure a smooth flow of milk through the orifice 106.

Overlying and completely surrounding the bowl 102 is a flexible membrane 107, held in place by any suitable means, such as a communicating portion of control section 101.

Control section 101 may be physically removed from section 100 but joined by any suitable communicating tube, or, as shown, physically made as a unitary assembly.

The adjacent portion of control section 101 can be slightly convex in form, and a tube 108 cut as a tunnel in the control section exits just behind flexible membrane 107. The other end of tube 108 terminates at orifice 109, to which vacuum is applied.

In addition, control section 101 anad valve section 100 may be used independently of each other, the former providing vacuum control in tube 108, the latter providing a valve action when a suitable source of vacuum replaces control section 101.

Communicating with tube 108 is an "on" control tube 110, which exits to the ambient air at orifice 111. Tube 110 is connected to orifice 109 via the front portion of valve chamber 112 and tube 108. Between the exit of valve chamber 112 and the orifice 109, a partial constriction 113 exists in tube 108.

Constriction 113 is large and represents a relatively large impedance to the flow of air compared to the restriction offered by tube 110 and orifice 111.

Centrally of the valve chamber 112 is a diaphragm 114, provided with means for blocking the exit of valve chamber 112 into tube 108 when the diaphragm 114 is flexed toward it. Diaphragm 114 also effectively seals the front part of chamber 112 from the rear.

Communicating with the rear portion of chamber 112 is "OFF" control tube 115, which exits to the ambient air at orifice 116. The rear portion of chamber 112 communicates with tube 108 between constriction 113 and orifice 109. A constriction 117 is provided in the tube connecting the rear of chamber 112 with tube 108.

Constriction 117 is large and represents a relatively large impedance to the flow of air compared to the restriction offered by tube 115 and orifice 116.

In operation, vacuum is applied to outlet orifice 104, as well as orifices 109 and 106. Since diaphragm 114 is centrally located, ambient air will be drawn through orifice 111, past the front of diaphragm 114, through the large orifice communicating between tube 108 and chamber 112, which substantially reduces the vacuum pressure in tube 108. Accordingly, a strong differential in pressure will occur across diaphragm 107, and it will be drawn into bowl 102, blocking orifice 104, channel 105, and orifice 106. Milking pressure is therefore stopped from reaching the teat of the cow, inhibiting any milking stress thereon.

When milking is to start, orifice 111 is blocked by, for instance, a finger. Air passing through tube 110 is stopped, and the pressure due to vacuum applied to orifice 109 draws diaphragm 114 against the exit of chamber 112 to tube 108. With blockage of orifice 111 released, diaphragm 114 is designed to maintain blockage of the exit of chamber 112 to tube 108, maintaining a differential of pressure across diaphragm 114. Vacuum pressure is thus maintained in tube 108.

With the initiation of vacuum pressure in tube 108, the pressure differential is removed from diaphragm 107, and indeed, a differential can occur in reverse. Diaphragm 107 is thus allowed to return to its normal position pressed against the adjacent portion of control section 101. The orifices 104 and 106 are thus released from being blocked, milking pressure is provided through to inlet orifice 103, and milking begins.

To stop milking pressure, orifice 116 is blocked, causing an equalization of vacuum pressure between both sides of diaphragm 114, and it springs back to its normal central location. This opens communication between the front of chamber 112 and tube 108, allowing ambient air to pass through tube 110, and substantially reduce the vacuum pressure in tube 108. A differential in pressure across diaphragm 107 occurs, and as described above, the diaphragm moves to block orifices 104 and 106.

It is preferred that a magnetic material be included within or attached to diaphragm 114. With this structure, a solenoid 118 located adjacent the diaphragm, when operated, can be caused to return it to its central location. It may be seen therefore that solenoid 118, when operated, will cause the stoppage of milking pressure on its corresponding teat.

Alternately solenoid 118 may be so placed that it causes a restriction to be placed into tube 115 thereby increasing vacuum preserve in the reserve portion of chamber 112 causing diaphragm 114 to move to its central location.

It may also be seen that a solenoid may be used in similar manner to control the "ON" function.

Solenoid 118 corresponds to one of solenoids 97A, 97B, 97C and 97C in FIG. 7, and consequently it may be seen that, as described earlier, a reduction in measured milk conductivity, after a predetermined time delay, will cause a corresponding solenoid to operate, which will automatically remove milking pressure from a corresponding teat, through the action of the just-described valve.

Accordingly, for a cow, four such valves will be necessary, four solenoids acting responsively if independent vacuum shutoff is required for each quarter. Alternatively, one valve can be employed to remove milking vacuum simultaneously from all quarters.

It is preferred that the body of the valve proper 100, and control section 101 be fabricated of non-contaminating material, with smooth internal edges so as to be easily cleaned and non-bacteria holding, such as polycarbonate. Diaphragms 107 and 114 should be flexible, non-contaminating, and durable, such as silicone rubber or neoprene.

In order to reduce the possibility of the ingress of dirt, the finger preferably should not be used to cover control orifices 111 and 116, but a mechanical blockage means should be used instead. A flexible membrane 119 can be provided, with rubber (or the like) blockage members 120 and 121, which are shaped to the same form as the surface of orifices 111 and 116. Accordingly, when blockage members 120 or 121 are depressed, they will substantially fill and block the ingress of air into the corresponding orifices. A frame 122 can hold the membrane in place.

Figure 8A:
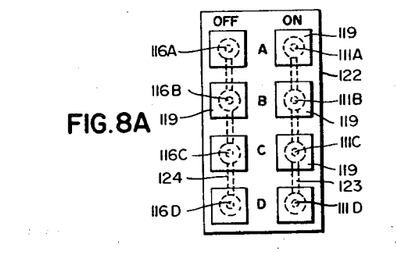

FIG. 8A shows in plan the frame 122, with four on and off controls for four valves, contained therein. Orifices 111A, 111B, 111C, and 111D are provided as on orifices for each of four valves, and orifices 116A, 116B, 116C, and 116D as off orifices for the same corresponding valves A, B, C, and D. Exposed is flexible membrane 119 adapted to be depressed momentarily, and manually depressed.

It may be seen that the structure described above provides means for detecting mastitis in milk during the milking process in a simple and automatic manner. Since immediate detection is apparent, therapy of the quarter can save substantial quantities of milk from contamination, resulting in a substantial saving to the milk producer. In addition, since automatic detection of the depletion of milk from a particular quarter is provided, and milking vacuum is automatically removed from the corresponding teat, physical and psychological stress of the animal is substantially reduced. As it is believed that such stress can sometimes reduce resistance of the animal to the onset of mastitis, the present invention can aid in resisting the disease. Since the output reading device can be in permanent record form, record keeping of milk yield, conductivity, etc. can be automatically stored in a computer or other data storage machine, as a record of health and milk production of the animal.

It should be noted that the apparatus should monitor milk at a uniform temperature so as to render the fluid's conductivity insensitive to differential thermal changes. It is found that the temperature of milk leaving the cow is sufficiently uniform. Thermistors can be added to the apparatus to determine the temperature of the milk as conductivity is measured, which readings can also be recorded with conductivity and/or conductivity ratio.

It will be obvious to one skilled in the art that numerous modifications, alternative structures, etc., can be provided. Such modifications, alternative recording systems, and alternative designs are contemplated by the inventors, and are considered part of this invention.

For instance, the invention need not be restricted to the multiplexing of the signals resulting only from the four quarters of one cow. The signals from numerous cows can be multiplexed together, and demultiplexed, grouped and the ratios or absolute value signals determined. Where other fluids than milk are measured, as many as required can be multiplexed, given the time division resolution desired.

Alternatively, the respective channels need not be multiplexed at all, and each being provided in parallel with the others to the ratio or absolute value signal determination circuitry described with reference to FIG. 7, or to individual dedicated circuitry for each channel.

Alternative signal coupling and detection means could also be used in place of the capacitive structure described, so long as it provides the required signal representative of the fluid parameter to be measured. For instance, a radio frequency signal could be applied to the respective fluid by inductive means, such as by the use of toroids. One such alternative detection means is described in U.S. Pat. No. 3,396,331.

The embodiments of the invention in which an exclusive property of privilege is claimed are defined as follows.

1. Apparatus for determining deviant conductivity of one or more fluids of a group of fluids from a selected conductivity value, comprising:
    a. first means for providing signals representative of the conductivity values of each fluid, and
    b. second means connected to said first means for comparing said signals and providing output signals representative of predetermined conductivity relationships, depending on the conductivity values, for the respective fluids.

2. Apparatus as defined in claim 1, in which said first means comprises signal pickup means for receiving electrical signals representative of the individual fluid conductivities of each of said fluids, and said second means comprises detecting means connected to the signal pickup means for producing a plurality of first signals having amplitudes representative of the conductivities of the respective fluids, and ratio determining means connected to the detecting means for producing second signals corresponding to the amplitude ratios of each of said first signals with respect to a selected one of said first signals whereby the conductivity ratios of each of said fluids can be determined.

3. Apparatus as defined in claim 2, in which said ratio determining means includes means for determining the first signal which represents the lowest valued conductivity of said fluids, the lowest valued of said first signals being designated as said selected one of said first signals.

4. Apparatus as defined in claim 3, in which the pickup means comprises a group of dielectric tubes each for passing individual fluids of the group of fluids therethrough, first conducting cylinders each surrounding and adjacent individual ones of said tubes, pairs of additional conducting cylinders similar to the first conducting cylinder surrounding and adjacent individual ones of said tubes on different sides of said first cylinder, at equally spaced positions and all electrically connected together, cylindrical shields of diameter greater than the said first cylinder individually coaxially positioned over, but insulated from each said first cylinder, the length of the shields extending at least approximately 25% of the length of said first cylinder on each side thereof.

5. Apparatus as defined in claim 3, in which said signal pickup means comprises a group of dielectric tubes through which individual fluid streams can flow, means for coupling electrical energy through each of the dielectric tubes and the fluid streams flowing therethrough, and means for coupling individual electrical signals passing through the tubes and fluid streams to the detecting means.

6. Apparatus as defined in claim 5, in which the pickup means further comprises a pair of capacitor plates located adjacent each of said tubes so as to incorporate the fluid flowing therethrough as capacitor dielectric.

7. Apparatus for detection of the conductivity of milk comprising:
    a. a group of dielectric tubes each through which milk emanating from the respective teats of a milk producing animal can pass,
    b. coupling means for coupling radio frequency electrical energy through the dielectric of each of the tubes and the milk,
    c. receiving means for receiving the respective signals resulting from passage of the radio frequency energy through the milk,
    d. detecting means for detecting the amplitudes of each of said respective signals, and for providing individual signals corresponding to each of said respective amplitudes, and indicative of corresponding milk conductivity in respective ones of said tubes, and
    e. means connected to said detecting means for determining the amplitude ratios of said individual signals with respect to one of said signals whereby the conductivity ratios of the milk passing through each of the dielectric tubes can be indicated.

8. Apparatus as defined in claim 7 in which said coupling means comprises a pair of conductive cylinders surrounding spaced lengths of each said dielectric tube, one of each of said pairs connected to ground and the other to a source of radio frequency signal; and said receiving means comprising a plurality of toroids: respective ones of which the individual signals which are passed through each respective dielectric tube are coupled.

9. Apparatus as defined in claim 7, further including means connected to said amplitude ratio determining means for providing a signal indicative of the conductivity of the milk flowing in a dielectric tube having fallen to a predetermined level, whereby milking vacuum applied to the corresponding teat having the reduction in conductivity in its milk may be cut off.

10. Apparatus as defined in claim 7, in which said amplitude ratio determining means comprises means for detecting the lowest amplitude said individual signal, and for determining the ratio of each of the other said individual signals to the lowest amplitude of said individual signal.

11. Apparatus as defined in claim 10, further including means for indicatng the presence of a ratio substantially deviant from the minimum ratio.

12. Apparatus as defined in claim 11, in which said coupling means comprises a pair of conductive cylinders surrounding spaced lengths of each said dielectric tube, one of each of said pairs connected to ground and the other to a source of radio frequency signal; and said receiving means comprising a plurality of toroids, respective ones of which the individual signals which are passed through each respective dielectric tube are coupled.

13. Apparatus as defined in claim 11, further including threshold means for detecting the presence of a conductivity value lower than a predetermined conductivity, and cut-off means connected to the threshold means for removing the means of holding the teat of said animal to the tube, corresponding to the below threshold conductivity value.

14. Apparatus as defined in claim 13, in which of cut-off means comprises
   a. a bowl having an inlet orifice and an outlet orifice, the outlet orifice being disposed at the bottom of the bowl, the inlet orifice adapted to be connected to the means of holding the teat of said animal, the outlet orifice adapted to be connected to a source of vacuum,
   b. a reservoir channel in the bottom of the bowl spaced from the outlet orifice, cut into the bottom of the bowl,
   c. a milk bypass tube communicating with the bottom of the reservoir channel, connected to one of said dielectric tubes,
   d. a diaphragm overlying the bowl, controlled by the threshold means, for closing the outlet orifice and reservoir channel upon the conductivity value dropping to a value lower than said predetermined conductivity.

15. Apparatus as defined in claim 14, in which the diaphragm covers the top of the bowl; further including a pneumatic tube communicating with the top of the diaphragm for applying pressure to the diaphragm whereupon it can close the outlet orifice, means for applying vacuum to the pneumatic tube at an inlet; a chamber having a front portion and a rear portion separated by a flexible membrane, the front portion communicating with the pneumatic tube via a communicating passage; an ON control tube communicating between the ambient air and the front portion of the chamber, and an OFF control tube communicating between the ambient air and the rear portion of the chamber, the diaphragm being adapted to close the communicating passage between the front of the chamber and the pneumatic tube upon the ON tube being blocked; a bypass tube communicating between the back portion of the chamber and the pneumatic tube between said communicating passage and the inlet to the pneumatic tube, and a partial constriction in the pneumatic tube between said communicating passage and the bypass tube entry.

16. Apparatus as defined in claim 15, further including means attractive to a magnet embedded in the flexible membrane, and a solenoid disposed adjacent the chamber adapted to be coupled to the means attractive to a magnet, connected to the threshold means.

17. Apparatus as defined in claim 15, further including solenoid means connected to the threshold means adapted to cut off communication to the ambient air of the ON or OFF control tubes under control of the threshold means.

18. Apparatus as defined in claim 15, in which the inlet orifice is disposed at an angle to the bowl, whereby the milk flowing therethrough is caused to swirl around the bowl, and in which the reservoir channel is annularly shaped, completely surrounding the outlet orifice.

19. Apparatus for detection of the conductivity of fluids comprising:
   a. a plurality of tubes through which the individual fluids can pass,
   b. means for applying a radio frequency signal to each tube in such manner as to pass through the individual fluids, resulting in individual signals of amplitude representative of the conductivity of each of the fluids,
   c. a radio frequency oscillator connected to the (b) means,
   d. multiplexing means for combining said individual signals in a predetermined manner, connected to the (b) means,
   e. detecting means for detecting the signal amplitude representative of the combined said individual signals,
   f. demultiplexing means connected to the detecting means for separating the detected said individual signals, from the combined said individual signals,
   g. comparing means for receiving said individual signals and determining the lowest amplitude one of said individual signals,
   h. dividing means connected to the detecting means and the comparing means for sequentially determining the ratio of the amplitudes of each of said detected individual signals with the amplitude of the lowest of said individual signals, and providing ratio signals,
   i. means for providing an output from the ratio signals, whereby a ratio deviating in value from the other ratios can be determined.

20. Apparatus as defined in claim 19, in which the comparing means comprises means for receiving said individual signals from the demultiplexing means on individual lines, and for gating said individual signals to an output line upon reception of an enable signal; means for comparing each of said individual signals whereby the lowest amplitude one of said individual signals is determined, and for producing an enable signal corresponding to the line carrying the lowest amplitude one of said individual signals, and means for applying the enable signal so as to gate the lowest amplitude signal to the output line, the output line being connected to the dividing means.

21. Apparatus as defined in claim 20, in which the multiplexer and demultiplexer operate in time division, a gate connected in the path between the dividing means and the detecting means, further including means connected to the multiplexer, demultiplexer and gate for enabling synchronous time division multiplexing, demultiplexing, and sequential gating of the combined detected said individual signal to the dividing means.

22. Apparatus as defined in claim 21, in which said (i) means comprises an output gate for receiving the ratio signals, means connecting the output gate and said means for enabling said time division and sequential gating whereby sequential gating of the output gate is provided, further including readout means connected to the output gate, whereby sequential and synchronous passage of individual ratio signals to the readout means is enabled.

23. Apparatus as defined in claim 21, further including means connected between said individual lines and the demultiplexing means for storing a representation of the individual detected said individual signals during the time intervals between time divisison signal pulses.

24. Apparatus as defined in claim 21, further including threshold means connected to said individual lines for detecting individual levels of conductivity lower than a predetermined conductivity, and fluid stop means connected to the threshold means for causing the cessation of the flow of fluid through the tube carrying the fluid having the conductivity lower than the predetermined conductivity.

25. Apparatus as defined in claim 24, in which said fluid stop means comprises means for shutting off the source of fluid only after a predetermined time delay.

26. Apparatus as defined in claim 25, in which the (a) and (b) means comprises, for each individual fluid, a dielectric tube for passing fluid therethrough, a first conducting cylinder surrounding and adjacent said tube, a pair of conducting cylinders similar to the first conducting cylinder surrounding and adjacent said tube on different sides of the first cylinder, at equally spaced positions, electrically connected together, a cylindrical guard shield of diameter greater than the first cylinder, coaxially positioned over, but insulated from, the first cylinder, the length of said shield extending at least about 25 percent of the length of the first cylinder on each side thereof; means for applying the radio frequency signal between all of the first cylinders, and all of the pairs of conducting cylinders in parallel, and means connecting all of the guard shields together and to ground.

27. Apparatus as defined in claim 26, in which the radio frequency signal is applied to each of the first cylinders through individual inductances, the multiplexing means being individually coupled to the individual inductances through secondary inductances in individual inductive relationship therewith.

28. Apparatus as defined in claim 27, further including a compensating inductance connected between the guard shield and the source of radio frequency signal, and a compensating capacitance connected between the guard shield and the pair of cylindrical shields, the pair of cylindrical shields being connected to ground with one terminal of the oscillator.

29. Apparatus as defined in claim 28, in which the compensating capacitance is comprised of a variable capacitor.

* * * * *

UNITED STATES PATENT OFFICE
CERTIFICATE OF CORRECTION

Patent No. 3,989,009  Dated November 2, 1976

Inventor(s) James D. J. Robar et al

It is certified that error appears in the above-identified patent and that said Letters Patent are hereby corrected as shown below:

Assignee should be indicated as:

--SED Systems Ltd., Canada--

Signed and Sealed this

Seventh Day of June 1977

[SEAL]

*Attest:*

RUTH C. MASON
*Attesting Officer*

C. MARSHALL DANN
*Commissioner of Patents and Trademarks*